United States Patent [19]

Gscheidmeier et al.

[11] Patent Number: 5,596,127
[45] Date of Patent: Jan. 21, 1997

[54] PROCESS FOR THE CONTINUOUS PREPARATION OF TERPENE ESTERS

[75] Inventors: Manfred Gscheidmeier, Gablingen; Rudolf Gutmann, Gersthofen; Jakob Wiesmüller, Stettenhofen; Alfred Riedel, Stadtbergen, all of Germany

[73] Assignee: Hoechst Aktiengesellschaft, Germany

[21] Appl. No.: 462,701

[22] Filed: Jun. 5, 1995

[30] Foreign Application Priority Data

Jun. 6, 1994 [DE] Germany .......................... 44 19 686.5

[51] Int. Cl.$^6$ ................................. C07C 9/52; C07C 7/02
[52] U.S. Cl. ............................................ 560/220; 560/249
[58] Field of Search ...................................... 560/220, 249

[56] References Cited

U.S. PATENT DOCUMENTS 4,855,488  8/1989  Gude ........................................ 560/249

FOREIGN PATENT DOCUMENTS 1196190  5/1962  Germany .
013158  2/1974  Japan .

OTHER PUBLICATIONS

Database WPI, Week 8318, Derwent Publications Ltd., London, GB; AN 83–42349 1983.
Database WPI, Week 7423, Derwent Publications Ltd., London, GB; An 74–42542 1974.
Database WPI, Week 7011, Derwent Publications Ltd., London, GB; AN 70–17979 1970.

*Primary Examiner*—Paul J. Killos
*Attorney, Agent, or Firm*—Connolly & Hutz

[57] ABSTRACT

In a process for preparing terpene esters by reaction of camphene and a low molecular weight carboxylic acid over an acid ion exchanger as catalyst, the reactants are passed from below through the acid ion exchanger located in a column-shaped reactor at such a velocity that the ion exchanger is suspended to uniformly fill the reactor, i.e. gives a pseudofluid suspended bed. In the case of the preparation of isobornyl acetate, a high specific catalyst productivity, a high selectivity of the reaction with formation of small amounts of other esters, a high degree of conversion of the reaction component used in substoichiometric amount and a high total catalyst productivity are achieved.

9 Claims, No Drawings

PROCESS FOR THE CONTINUOUS PREPARATION OF TERPENE ESTERS

The invention relates to an improved process for preparing terpene esters over a solid catalyst.

It is known that camphene and acetic acid in a molar ratio of 1:5.7 can be allowed to run continuously at 60° C. over a fixed bed of cation exchange resin to give good yields of ester (cf. Russian Patent 102 445).

Furthermore, a process is known in which camphene and acetic acid are reacted in equimolar amounts in a batch-wise or continuous process in the presence of an acid ion exchange resin (cf. JP 49-13158).

The use of sulfonic acid ion exchangers comprising styrene-divinylbenzene copolymers for reacting camphene and acetic acid in the presence of a fluidized catalyst is also known (cf. DD 69586).

The previous use of acid ion exchange resins was in laboratory experiments in which, owing to the small volumes, there are no problems with mass transfer and dissipation of heat. If the method is transferred to industrial scale production apparatus, substantially higher demands are placed on control of product flow and constancy of temperature than is the case for small experimental apparatus:

1. The reaction is exothermic to the extent of about 3 kcal/mol.
2. With regard to the camphene conversion, it proceeds only to an equilibrium position which depends very largely on temperature, mixing ratio and purity of the reactants and also on the quality and amount of the catalyst.
3. Depending on the temperature, catalyst activity and residence time, there is formation of other esters, such as pseudobornyl acetate, isofenchyl acetate or α-fenchyl acetate, from camphene and tricyclene (an isomer always present) but also by isomerization of isobornyl acetate already formed. Owing to their characteristic odor, these other esters lead, when present in concentrations above very low limits, to an undesired deviation in the overall odor of the fragrance isobornyl acetate.

For these reasons, decisive factors for the yield and quality of the target product are:

uniformly good dissipation of heat;

uniform product flow over the entire width and height of the catalyst bed;

a residence time which is as short as possible.

In the reactions described hitherto, attention is always paid only to the total activity, but not at all to the lower selectivity of ester formation which is caused, in the case of a fluidized bed, primarily by non-uniform residence time and in the case of a fixed bed additionally by less favorable temperature distribution.

It has now been found that these disadvantages can be avoided by carrying out the reaction in a floating catalyst bed.

The invention thus provides a process for preparing terpene esters by reaction of $C_{10}H_{16}$-terpenes and a low molecular weight carboxylic acid over an acid ion exchanger as catalyst, which comprises carrying out the reaction at a molar ratio of terpene to carboxylic acid of from 0.2:1 to 2:1 and a temperature of from 25° to 60° C., with the reactants being passed from below through the acid ion exchanger located in a tubular reactor at such a velocity that the ion exchanger is suspended to uniformly fill the reactor.

In the process of the invention, a terpene hydrocarbon is reacted with a low molecular weight carboxylic acid.

Suitable terpenes are $C_{10}H_{16}$ hydrocarbons, in particular camphene which can contain up to about 20% of tricyclene.

Suitable low molecular weight carboxylic acids are saturated or unsaturated carboxylic acids having from 1 to 5 carbon atoms, in particular acetic acid or methacrylic/acrylic acid.

The reactants are used in a molar ratio of terpene to acid of from 0.2:1 to 2:1, in the case of saturated acids preferably from 0.2:1 to 0.3:1, in the case of unsaturated acids preferably from 1:1 to 2:1.

The reaction temperature is selected so as to be high enough for the liquid reactants to react sufficiently with one another; it is from 25° to 60° C., preferably from 28° to 55° C. The pressure is from 1 to 2 bar, preferably from 1 to 1.3 bar.

The reactor used for the process of the invention is a vertically positioned, cylindrical reactor which should have a capacity of from 200 to 500 dm³, preferably up to 350 dm³, and a ratio of height to diameter of from 16:1 to 19:1. At both the bottom and the top the reactor has a sieve tray having a sufficiently small mesh opening to prevent the particulate ion exchanger from escaping either upwards or downwards. The ion exchanger is charged into and discharged from the reactor through specific lines. To make the flow uniform, the inlet sieve, which is configured as a support tray, can be supplemented in places by internal fittings such as cover plates or guide plates.

The reactor is charged with such an amount of acid ion exchanger in the form of small spheres that, after swelling by the reactants, the reactor still has a free volume of from 20 to 40%. Suitable ion exchangers are the commercial cation exchangers, which are more or less moist with water, preferably sulfonic acid copolymers of styrene and divinylbenzene in the form of small spheres, for example ®Amberlyst 15, ®Bayer K 2611, ®Purolite 175 CT or the like. The commercial ion exchangers, preferably sulfonic acid copolymers of styrene and divinylbenzene having a macroporous structure, contain some water and are therefore, prior to carrying out the reaction, first swelled in the reactor using acetic acid/isobornyl methacrylate and then "dried" with added anhydride of the acid to be used down to a water content (in the liquid) of under 0.1%.

Reaction mixture is then fed in from below through the sieve tray at an appropriately selected velocity in such a way that the ion exchanger, owing to the moderate density difference between it and the liquid, is set into gentle floating motion. However, it is here not simply pushed upwards or fluidized in the reactor, but rather it is "expanded", depending on the flow velocity through the reactor, more or less over the entire reactor height, so that it is brought from bottom to top into a pseudofluid suspended state. To achieve this, the height/cross-section ratio of the reactor, the ion exchanger volume and the amount of mixture to be passed through have to be matched exactly to one another. At the same time, the residence time of the reactants is selected in such a way that the desired conversion at the selectivity required is achieved. The ideal suspended state is reached when the upper surface, which is rotating slightly but appears relatively flat, of the "expanded" catalyst bed extends to just below the outlet sieve of the reactor. In this operating state the catalyst motion is so gentle that no abrasion whatsoever is observed.

The water content of the reaction mixture to be passed through is preferably set to a value below 0.05%, for example by addition of the necessary amount of the anhydride of the acid used. The reaction with the water present can occur either in the reactor itself or outside the reactor.

The fully continuous throughput is only interrupted when activity and selectivity are no longer sufficient at relatively high temperatures. Subsequently, the ion exchanger in the reactor can be, if desired, first rinsed with acetic acid, then freed at elevated temperature from the deposits of resin-like residues using an organic solvent, for example ethanol, and can then be used again for the reaction. These cycles can be carried out a plurality of times, but the catalyst operating time becomes somewhat shorter each time.

If the catalyst, aged by coating with resin, becomes compacted, the uniform suspension of the catalyst in the liquid can be restored by additional measures, such as brief blowing in of nitrogen, light pulsation impulses into the reaction mixture, brief variation of the flow velocity or the like. The installation of slowly rotating stirrers is also conceivable.

In the preparation, for example, of isobornyl acetate from camphene and acetic acid, the reaction proceeds only to a temperature-dependent equilibrium state; it is therefore useful to commence the reaction at from 25° to 27° C. and to increase the temperature slowly to about 50° C. as activity loss gradually occurs (as a result of formation of resinous products). Although the higher temperature improves the activity of the catalyst, it leads to selectivity loss as a result of increased formation of interfering "other esters", such as isofenchyl acetate and pseudobornyl acetate.

Technical-grade camphene always contains tricyclene which likewise promotes the formation of said other esters. Its content in the camphene should therefore be, if possible, below 18%. The lower this value, the higher the temperature which can be selected to achieve the same selectivity but a higher degree of conversion.

The optimum molar ratio of acetic acid: camphene is from 3.5:1 to 4.5:1, since in this way a favorable influence is exerted both on the equilibrium reaction and on the viscosity and density of the reaction mixture for setting the suspended state of the catalyst. At the same time, the acid excess is just sufficient for the unreacted terpene hydrocarbons to subsequently be azeotropically distilled off almost quantitatively.

The process of the invention brings further improvements compared with the known procedures for preparing terpene esters:

- high specific catalyst productivity of, for example, 2.1 kg of isobornyl acetate/dm³ of catalyst/h;
- high selectivity of the reaction with formation of only about 5.5% of other esters;
- high degree of conversion of on average 80% of the camphene;
- high total catalyst productivity on 1st use at almost 700 kg of isobornyl acetate/dm³ of catalyst.

Each one of these values can be improved by changing the reaction conditions, but a worsening of other values has to be accepted. (The following example is to illustrate the invention.)

In the preparation, for example, of isobornyl methacrylate from camphene and methacrylic acid, the formation of "other esters" is somewhat less critical, so that the reaction is carried out at from 45° to 60° C. Since higher residence time, i.e. lower throughput amount per unit time, is additionally required, the pseudofluid suspended state of the catalyzing ion exchange resin can be achieved only by either a correspondingly slimmer reactor and higher flow velocity or using a normally dimensioned reactor if the reaction mixture is at the same time circulated by pumping. The latter has the great advantage that the suspended state of the catalyst can be kept constant independently of the feed amount, i.e. independently of the residence time.

Isobornyl methacrylate too is formed in an equilibrium reaction. Since unreacted methacrylic acid here very easily tends to polymerize, the acid concentration is kept as small as possible by means of the selected molar ratio of camphene to methacrylic acid of from 2:1 to 1:1. In addition, the suspended catalyst bed is here of great advantage, since there are no motion-free zones (as for example in the fixed bed system) which increase the danger of polymerization.

EXAMPLE 1

A cylindrical reactor having an empty volume of 220 dm³, which was fitted with a plurality of mutually independent cooling coils (in each case in a double configuration), was charged with 130 dm³ of an acid ion exchanger based on styrene/divinylbenzene (®Amberlyst 15 dry, Rohm and Haas) and the resin was swelled using acetic acid with addition of acetic anhydride. Subsequently, a mixture of 310 dm³ of camphene (containing on average 17.5% of tricyclene) and 440 dm³ of acetic acid was continuously metered into the reactor from below. If necessary, sufficient acetic anhydride was fed in to keep the water content in the raw mixture below 0.05%. The reaction temperature was, by means of cooling, first maintained at from 28° to 29° C., then gradually increased to 48° C. over the course of 14 days. In addition, the total throughput was reduced to 700 dm³/h after 7 days. With progressive aging of the catalyst, this was occasionally loosened up by brief feeding in of nitrogen.

The degree of camphene conversion achieved was on average 80%, the product purity, based on all ester components, was 94.4% of isobornyl acetate+0.3% of bornyl acetate. The subsequent distillation gave a total of 89 metric tons of isobornyl acetate in fragrance quality having a total ester content of 99.6–99.8%. The catalyst productivity was thus, in 14 days, 685 kg of pure product per dm³ of catalyst.

EXAMPLE 2

About 1.5 dm³ of isobornyl methacrylate were placed in a cylindrical reaction tube (glass) (d=65 mm, h=900 mm) fitted with double jacket and bottom frit, and were admixed with 1.5 dm³ of Amberlyst 15 dry (Rohm and Haas). After the swelling of the catalyst was complete, a reaction mixture comprising technical-grade camphene and methacrylic acid in a molar ratio of 1.5:1 plus 0.02% of phenothiazine as stabilizer was added from below until circulation of the mixture through the catalyst became possible. The circulation velocity was then adjusted so that the catalyst bed was expanded to from 1.5 to 2 times its volume. Subsequently, the reactor was brought to a temperature of from 45° to 50° C. by heating via a heat exchanger built into the circuit and by means of warm water in the double jacket, before continuous feeding in of further reaction mixture was commenced. The internal reactor temperature was then kept constant at 50° C. At a feed rate of 1 dm³ of reaction mixture per hour, the same amount was taken from the circulation system via an upswept overflow as crude product for subsequent distillation; it contained about 30% of terpene hydrocarbons, about 65% of esters and about 5% of residual acid.

Over the course of about 50 hours, only a small activity loss was observed, which could be compensated for by increasing the temperature. Turbidity due to polymer formation did not occur. Even afterwards, the crude product was very stable and could be separated by vacuum distillation to give a camphene-excess fraction (containing less acid) and an ester fraction containing 98–99% of esters (of which about 88% was isobornyl methacrylate).

When purer camphene is used, the isobornyl methacrylate content increases, depending on the content of residual tricyclene which is always present in the camphene, to up to about 95%.

We claim:

1. A process for preparing terpene esters by reaction of $C_{10}H_{16}$-terpenes and a low molecular weight carboxylic acid over an acid ion exchanger as catalyst, which comprises carrying out the reaction at a molar ratio of terpene to carboxylic acid of from 0.2:1 to 2:1 and a temperature of from 25° to 60° C., with the reactants being passed from below through the acid ion exchanger located in a column-shaped reactor at such a velocity that the ion exchanger is suspended essentially to uniformly fill the reactor.

2. The process as claimed in claim 1, wherein the terpene is a camphene containing tricyclene.

3. The process as claimed in claim 1, wherein the column-shaped reactor is vertically positioned.

4. The process as claimed in claim 3, wherein the acid ion exchanger is particulate and is caused to float by the reactants passing through the column-shaped reactor from below; the column-shaped reactor is provided with an overflow; the terpene and the carboxylic acid are continuously metered into said column-shaped reactor from below; a crude product containing a terpene ester is removed from said overflow; and said terpene ester is recovered from said crude product by distillation.

5. The process as claimed in claim 3, wherein the ratio of height to diameter of said column-shaped reactor ranges from 16:1 to 19:1.

6. The process as claimed in claim 1, wherein said carboxylic acid is saturated or unsaturated and has from 1 to 5 carbon atoms.

7. The process as claimed in claim 6, wherein said carboxylic acid is acetic acid, methacrylic acid, or acrylic acid.

8. The process as claimed in claim 7, wherein, when said carboxylic acid is acetic acid, the reaction is commenced at a temperature of 25° to 27° C., and the temperature is then increased to at least about 50° C.; or, when said acid is methacrylic acid, the reaction is carried out at from 45° to 60° C.

9. The process as claimed in claim 6, wherein said molar ratio is in the range of 0.2:1 to 0.3:1, when said carboxylic acid is saturated, and is in the range of 1:1 to 2:1, when said carboxylic acid is unsaturated.

* * * * *